(12) United States Patent
Masuda et al.

(10) Patent No.: US 7,339,041 B2
(45) Date of Patent: *Mar. 4, 2008

(54) OLIGONUCLEOTIDES AND METHOD FOR CHARACTERIZING AND DETECTING GENOGROUP II TYPE SMALL ROUND STRUCTURED VIRUS

(75) Inventors: Noriyoshi Masuda, Tokyo (JP); Takahiko Ishiguro, Yokohama (JP); Juichi Saito, Yamato (JP); Toshiki Taya, Sagamihara (JP); Kiyoshi Yasukawa, Kawasaki (JP)

(73) Assignee: Tosoh Corporation, Shinnanyo-shi (JP)

( * ) Notice: Subject to any disclaimer, the term of this patent is extended or adjusted under 35 U.S.C. 154(b) by 480 days.

This patent is subject to a terminal disclaimer.

(21) Appl. No.: 10/441,126

(22) Filed: May 20, 2003

(65) Prior Publication Data

US 2003/0180894 A1   Sep. 25, 2003

Related U.S. Application Data

(62) Division of application No. 09/989,002, filed on Nov. 21, 2001, now Pat. No. 6,630,300.

(30) Foreign Application Priority Data

Nov. 21, 2000 (JP) .............................. 2000-359482
Jan. 29, 2001 (JP) .............................. 02001-20231

(51) Int. Cl.
  *C07H 21/04* (2006.01)
(52) U.S. Cl. .................................................. 536/23.1
(58) Field of Classification Search ............... 536/23.1; 435/91.2, 91.21
See application file for complete search history.

(56) References Cited

U.S. PATENT DOCUMENTS 6,630,300 B2 * 10/2003 Masuda et al. ................ 435/5
2002/0031760 A1    3/2002 Saito et al.

FOREIGN PATENT DOCUMENTS

JP    2000 300297 A  * 10/2000
WO    WO 94/05700       3/1994

OTHER PUBLICATIONS

Sequence alignement of SEQ ID No. 1 fragments with Geneseq accession No. AAC929988 and AAC92999, submitted Mar. 27, 2001 in JP200030297-A.*
Sequence alignment of SEQ ID No. 1 fragments with catngs.seq database accession No. AAQ56831 and AAQ56829 of WO 94 05700-A2 published Mar. 17, 1994.*
Sequence alignment of SEQ ID No. 1 fragments with catngs.seq database accession No. AAV49284 of FR2751223-A1, published Jan. 23, 1998.*
Sequence alignment of SEQ ID No. 1 fragments with catngs.seq database accession No. AX03861 of WO 98/56929-A1, published Dec. 17, 1998.*
Le Guyader et al., Detection and analysis of a small round structured virus strain in oysters implicated in an outbreak of acute gastroenteritis, 1996, Applied and Environmental Microbiology, 62(11): 4268-4272.*
Lees et al., Detection of Small Round Structured Viruses in Shellfish by Reverse Transcription-PCR, 1995, Applied and Environmental Microbiology, 61(12): 4418-4424.*
Young et al., Transcription of cRNA for in situ hybridization from polymerase chain reaction-amplified DNA, 1991, Laboratory Investigation, 64(5): 709-712.*
CD-ROM containing an unbridged electronic version of the article on the "Preparaion and Utilization of Isolated and Purified Oligonucleotides" by Dr. Andrew Chin.
Jiang, X, et al., "Norwalk Virus Genome Cloning and Characterization", Science, vol. 250, No. 4987 (1990), pp. 1580-1583.
Vinje. J., et al., Genetic polymorphism across regions of the three open reading frames of "Norwalk-like viruses", Archives of Virology, vol. 145, No. 2, (2000), pp. 223-241.
Kievits. T, et al., "Nasba TM Isothermal Enzymatic In Vitro Nucleic Acid Amplification Optimized for the Diagnosis of HIV-1 Infection", Journal of Virological Methods, vol. 35, No. 3, (Dec. 1, 1991), pp. 273-286.
Ishiguro, et al., "Flourescence detection of specific sequence of nucleic acids by oxazole yellow-linked oligonucleotides. Homogenous quantitative monitoring of in vitro transcription", Nucleic Acids Research, vol. 24, No. 24, (1996), pp. 4992-4997.
Takahiko Ishiguro, et al. Nucleic Acids Research, vol. 24, No. 24, pp. 4992-4997, "Fluorescence Detection of Specific Sequence of Nucleic Acids by Oxazole Yellow-Linked Oligonucleotides. Homogeneous Quantitative Monitoring of in Vitro Transcription" 1996.
Dingle et al. sequence alignment of SEQ ID No. 20 with GenEmbl accession No. X86557 from Journal of General Virology, 1995; 76 (9), 2349-2355.
Cauchi et al. sequence alignment of SEQ ID No. 28 with GenEmbl accession No. U46500 from Journal of Medical Virology, 1996; 49 (1): 70-76.
Green et al. sequence alignment of SEQ ID No. 35 with GenEmbl accession No. X76716 from Journal of General Virology.
U.S. Appl. No. 10/441,126, filed May 20, 2003, Masuda, et al.
U.S. Appl. No. 10/391,631, filed Mar. 20, 2003, Yusukawa, et al.

* cited by examiner

*Primary Examiner*—Bruce R. Campell
*Assistant Examiner*—Nicole E Kinsey
(74) *Attorney, Agent, or Firm*—Oblon, Spivak, McClelland, Maier & Neustadt, P.C.

(57) ABSTRACT

Nucleic acid sequences, oligonucleotides and a method for detection of SRSV, in particular, a virus which belongs to Genotype II (GII), in clinical examinations, public health examinations, food evaluations and food poisoning examinations are provided.

6 Claims, 5 Drawing Sheets

(A)
FLUORESCENCE PROFILE

(B)
CALIBRATION CURVE

OLIGONUCLEOTIDES AND METHOD FOR CHARACTERIZING AND DETECTING GENOGROUP II TYPE SMALL ROUND STRUCTURED VIRUS

The present application is a divisional application of U.S. Ser. No. 09/989,002 filed Nov. 21, 2001, now U.S. Pat. No. 6,630,300.

FIELD OF THE INVENTION

SRSV (Small Round Structured Virus) is commonly known as a causative virus of viral food poisoning. The present invention relates to nucleic acid sequences, oligonucleotides and method for detection of SRSV and, in particular, a virus which belongs to Genotype II (GII) in clinical examinations, public health examinations, food evaluations and food poisoning examinations.

PRIOR ART

SRSV belongs to the human Calicivirus group. Human Caliciviruses are classified according to their three genetic types: Genogroup I (GI), Genogroup II (GII) and Genogroup III (GIII). Generally speaking, GI and GII Caliciviruses are generally referred to as SRSV, and GIII Caliciviruses are referred to as human Caliciviruses in the narrow sense.

Approximately 20% of the food poisoning cases reported in Japan are attributed to viral causes. SRSV is detected in over 80% of these viral food poisoning cases. The major source of infection is food, and raw oysters are often implicated. SRSV has also been detected in infant (sporadic) acute enterogastritis, thus suggesting the possibility of propagation from human to human. SRSV detection therefore provides an important contribution to public health and food quality.

To date, SRSV detection has been relied on electron microscope observation. Detection by this method, however, requires the virus to be present in an amount of $10^6$/ml or greater, and thus the detection subject was limited to patient's feces. Further, even though observation of the virus was possible, it could not be identified.

In recent years, it has become possible to produce viroid hollow particles for human caliciviruses, and research is advancing toward a specific antibody-detecting ELISA employing such particles. However, the detection sensitivity is still on the same level as electron microscopy, and the method is therefore far from highly sensitive.

As mentioned above, since a complex procedure and a long time are required for the conventional method and it is difficult to detect trace amounts of SRSV in samples within a short time, it has been desired to provide a detection method satisfying the high-speed and high-sensitivity requirements for food evaluation and the like. There has also been a demand for development of an automated examination device which allows more convenient examination.

Methods of amplifying target nucleic acid can be utilized as highly sensitive detection methods. One known method for amplification of specific sequences of genomic RNA such as that of SRSV is the reverse transcription-polymerase chain reaction (RT-PCR). This method comprises synthesis of a cDNA for the target RNA by a reverse transcription step, and then repeating a cycle of heat denaturation, primer annealing and extension reaction in the presence of a pair of primers which are complementary and homologous to both ends of specific sequences of the cDNA (the antisense primer may be the one used in the reverse transcription step) as well as a thermostable DNA polymerase, thereby amplifying the specific DNA sequence. However, the RT-PCR method requires a two-step procedure (a reverse transcription step and a PCR step), as well as a procedure involving rapidly increasing and decreasing the temperature, which prevent its automation.

Other methods known for amplification of specific RNA sequences include the NASBA and 3SR methods which accomplish amplification of specific RNA sequences by the concerted action of reverse transcriptase and RNA polymerase. In these methods, the target RNA is used as a template in the synthesis of a promoter sequence-containing double-stranded DNA using a promoter sequence-containing primer, reverse transcriptase and Ribonuclease H; this double-stranded DNA provides a template in the synthesis of an RNA containing the specific base sequence of the target RNA using an RNA polymerase; subsequently, this RNA provides a template in a chain reaction for synthesizing a double-stranded DNA containing the promoter sequence.

Thus, the NASBA and 3SR methods allow nucleic acid amplification at a constant temperature and are therefore considered suitable for automation. However, as these amplification methods involve relatively low temperature reactions (41° C., for example), the target RNA forms an intramolecular structure which inhibits binding of the primer and may reduce the reaction efficiency. Therefore, they require subjecting the target RNA to heat denaturation before the amplification reaction so as to destroy the intramolecular structure of the target RNA and thus to improve the primer binding efficiency. Further, even when carrying out the detection of an RNA at a lower temperature, these methods require an oligonucleotide capable of binding to the RNA forming such a molecular structure.

Thus, an object of the present invention is to provide nucleic acid sequences, oligonucleotides or suitable combination thereof, capable of specifically cleaving or amplifying SRSV and, in particular, a virus which belongs to GII type, preferably at a relatively low and constant temperature (between 35° C. and 50° C., preferably 41° C.), useful in detecting and identifying such a virus at high sensitivity.

DETAILED DESCRIPTION OF THE INVENTION

One embodiment of the invention relates to a cDNA as shown in SEQ. ID. No. 1, or fragment or derivative thereof having a size sufficient to bind to Genogroup II type Small Round Structured Virus (SRSV).

Another embodiment of the invention is an oligonucleotide for detection of GII type SRSV, which oligonucleotide is capable of binding to said GII type SRSV at specific site, and comprises at least 10 contiguous bases of any of the sequences listed as SEQ. ID. Nos.2 to 9.

In one aspect of the invention the oligonucleotide is an oligonucleotide probe for cleaving said RNA at said specific site by binding to said specific site of said RNA.

In another aspect of the invention, the oligonucleotide is an oligonucleotide primer for a DNA elongation reaction.

In another aspect of the invention, the oligonucleotide is an oligonucleotide probe a portion of which is modified or labeled with a detectable marker.

In another aspect of the invention, the oligonucleotide is a synthetic oligonucleotide in which a portion of its base(s) is (are) modified without impairing the function of said oligonucleotide as an oligonucleotide probe.

The oligonucleotides of the present invention, which have been accomplished to achieve the aforementioned object, are oligonucleotides that complementarily bind in a specific manner to intramolecular structure-free regions of the target RNA in the aforementioned RNA amplification, and they are capable of binding specifically to the target RNA without the heat denaturation described above. In this manner, the present invention provides oligonucleotides that bind to intramolecular structure-free regions of the GII type SRSV RNA at a relatively low and constant temperature (35-50° C., and preferably 41° C.), which are useful for specific cleavage, amplification, detection or the like of GII type SRSV RNA. More specifically, the present invention relates to an oligonucleotide primer which cleaves the target RNA mentioned above at specific site, an oligonucleotide primer for amplifying the above target DNA with PCR, an oligonucleotide primer for amplifying the above target DNA with NASBA or the like, and an oligonucleotide probe for detecting the target nucleic acid without or after these amplifications, thereby accomplishes rapid and highly sensitive detection.

SEQ ID Nos. 2 through 9 illustrate examples of the oligonucleotides of the present invention useful in cleavage, amplification, detection or the like of RNA derived from GII type SRSV. In this connection, RNA derived from GII type SRSV also includes RNA that has been produced by using these genes as templates. Although each of the oligonucleotide of the present invention may include entire base sequence of any of SEQ ID Nos.2 to 9, since 10 contiguous bases are adequate for specific binding to GII type SRSV, these oligonucleotides can be oligonucleotides comprising at least 10 contiguous bases of the described sequences.

The oligonucleotides of the present invention can be, for example, used as an RNA-cleavable probe. Cleavage of a target RNA at a specific site can be accomplished by hybridizing the oligonucleotide of the present invention to a single-stranded target RNA, and then exposing it to an enzyme which cleaves only the RNA moieties of the heteronucleic double-stranded RNA-DNA. As for this enzyme, those which are known to have common ribonuclease H activity can be used.

The oligonucleotides of the present invention can be used, for example, as oligonucleotide primers for nucleic acid amplification. If a nucleic acid amplification method is carried out using the oligonucleotide of the present invention as the primer, only the target nucleic acid, namely nucleic acids of the GII type SRSV, can be amplified. Although examples of amplification methods include PCR, LCR, NASBA and 3SR, nucleic acid amplification methods that can be carried out at a constant temperature such as LCR, NASBA and 3SR are particularly preferable. GII type SRSV can be detected by detecting the amplification product by various methods. In this case, any of the above oligonucleotides other than the oligonucleotide used in the amplification may be used as probes, and the fragment of the amplified specific sequence can be confirmed by electrophoresis or the like.

The oligonucleotides of the present invention can be used as probes by, for example, modifying its portion or labeling it with a detectable marker. When detecting the target nucleic acid, the oligonucleotide of the present invention labeled with the detectable marker may be hybridized to a single-stranded target nucleic acid, after which the hybridized probe can be detected via the marker. The marker detection may be carried out by a method suitable for the particular marker and, for example, when using an intercalator fluorescent dye for labeling the oligonucleotide, a dye with the property of exhibiting increased fluorescent intensity by intercalation in the double-stranded nucleic acid comprising the target nucleic acid, and the oligonucleotide probe, may be used in order to allow easy detection of only the hybridized probe without removal of the probe that has not hybridized to the target nucleic acid. When using a common fluorescent dye as the marker, the marker may be detected after removal of the probe that has not hybridized to the target nucleic acid. For the detection, the target nucleic acid in the sample is preferably amplified to a detectable amount by a nucleic acid amplification method such as PCR, NASBA or 3SR method, among which isothermal nucleic acid amplification methods such as the NASBA and 3SR methods are most preferable. When incorporating the nucleotide-labeled probe in the reaction solution during the amplification, it is especially preferable to modify the probe by, for example, adding glycolic acid to the 3'-end so that the probe will not function as a nucleotide primer.

One embodiment of the invention relates to a GII type SRSV RNA amplification process in which the specific sequence of said GII type SRSV RNA present in a sample is used as a template for synthesis of a cDNA employing an RNA-dependent DNA polymerase, the RNA of the formed RNA/DNA hybrid is decomposed by Ribonuclease H to produce a single-stranded DNA, said single-stranded DNA is then used as a template for production of a double-stranded DNA having a promoter sequence capable of transcribing RNA comprising said specific sequence or the sequence complementary to said specific sequence employing a DNA-dependent DNA polymerase, said double-stranded DNA produces an RNA transcription product in the presence of an RNA polymerase, and said RNA transcription product is then used as a template for cDNA synthesis employing said RNA-dependent DNA polymerase, wherein said RNA amplification process being characterized by employing a first primer comprising at least 10 contiguous bases, of any of the sequences listed as SEQ. ID. No. 20 to No. 24, which has a sequence homologous to a portion of said GII type SRSV RNA to be amplified, and a second primer comprising at least 10 contiguous bases, of any of the sequences listed as SEQ. ID. No. 25 to No. 31, which has a sequence complementary to a portion of said GII type SRSV RNA sequence to be amplified (where either or both the first and second primers include the RNA polymerase promoter sequence at their 5' end).

In one embodiment, the RNA amplification process is carried out in the presence of an oligonucleotide probe capable of specifically binding to the RNA transcription product resulting from the amplification and labeled with an intercalator fluorescent pigment, and changes in the fluorescent properties of the reaction solution are measured (with the proviso that said labeled oligonucleotide is different from said first oligonucleotide and said second oligonucleotide).

In one embodiment, the probe is designed so as to complementarily bind with at least a portion of the sequence of the RNA transcription product, and the fluorescent property changes relative to that of a situation where a complex formation is absent.

In one embodiment, the probe comprises at least 10 contiguous bases of any of the sequences listed as SEQ. ID. No. 32 to No. 35 or its complementary sequence.

The present invention provides a nucleic acid amplification process for amplification of GII type SRSV RNA in a sample, and a detection method for RNA transcription products obtained by the nucleic acid amplification process. The amplification process of the invention includes the PCR, NASBA and 3SR methods, but is preferably a constant temperature nucleic acid amplification method such as the NASBA or the 3SR methods whereby GII type SRSV-specific RNA sequences are amplified by the concerted action of reverse transcriptase and RNA polymerase (a reaction under conditions in which reverse transcriptase and RNA polymerase act in concert).

For example, the NASBA method is an RNA amplification process in which the specific sequence of GII type SRSV RNA present in a sample is used as a template for synthesis of a cDNA employing an RNA-dependent DNA polymerase, the RNA of the formed RNA/DNA hybrid is decomposed by Ribonuclease H to produce a single-stranded DNA, the single-stranded DNA is then used as a template for production of a double-stranded DNA having a promoter sequence capable of transcribing RNA comprising the specific sequence or the sequence complementary to the specific sequence employing a DNA-dependent DNA polymerase, the double-stranded DNA produces an RNA transcription product in the presence of an RNA polymerase, and the RNA transcription product is then used as a template for cDNA synthesis employing the RNA-dependent DNA polymerase, and the process of the present invention is characterized by employing a first primer comprising at least 10 contiguous bases of any of the sequences listed as SEQ. ID. No. 20 to No. 24 which has a sequence homologous to a portion of the GII type SRSV RNA, and a second primer comprising at least 10 contiguous bases of any of the sequences listed as SEQ. ID. No. 25 to No. 31, which has a sequence complementary to a portion of the GII type SRSV RNA sequence to be amplified (where either or both the first and second primers include the RNA polymerase promoter sequence at their 5' region).

While there are no particular restrictions on the RNA-dependent DNA polymerase, the DNA-dependent DNA polymerase and the Ribonuclease H, AMV reverse transcriptase which has all of these types of activity is preferred. The RNA polymerase is also not particularly restricted, but T7 phase RNA polymerase and SP6 phage RNA polymerase are preferred.

In this amplification process, there is added an oligonucleotide which is complementary to the region adjacent and overlapping with the 5' end of the specific sequence region (bases 1 to 10) of the GII type SRSV RNA sequence, and the GII type SRSV RNA is cleaved (with Ribonuclease H) at the 5' end region of the specific sequence to prepare the initial template for nucleic acid amplification, thereby allowing amplification of GII type SRSV RNA without the specific sequence at the 5' end. The oligonucleotide used for this cleaving may, for example, be any of those of SEQ. ID. No. 25 to No. 31 (provided that it differs from the ones used as the first oligonucleotide in the amplification process). The cleaving oligonucleotide is preferably chemically modified (for example, aminated) at the 3' hydroxyl in order to prevent an extension reaction at the 3' end.

The RNA amplification product obtained by the aforementioned nucleic acid amplification process may be detected by a known detection method but, preferably, the amplification process is carried out in the presence of an oligonucleotide probe labeled with an intercalator fluorescent pigment, while measuring the changes in the fluorescent properties of the reaction solution. The oligonucleotide probe will typically be the one wherein the intercalator fluorescent pigment is bonded to a phosphorus atom in the oligonucleotide by way of a linker. With this type of suitable probe, formation of a double strand with the target nucleic acid (complementary nucleic acid) causes the intercalator portion to intercalate in the double-stranded portion resulting in a change in the fluorescent property, so that no separatory analysis is necessary (Ishiguro, T. et al. (1996), Nucleic Acids Res. 24(24) 4992-4997).

The probe sequence is not particularly restricted so long as it has a sequence complementary to at least a portion of the RNA transcription product, but it is preferably a sequence comprising at least 10 contiguous bases of the sequences listed as SEQ. ID. Nos.32 to No. 35. Also, chemical modification (for example, glycolic acid addition) at the 3' end hydroxyl group of the probe is preferred in order to prevent an extension reaction with the probe as a primer.

Accordingly, it is possible to amplify and detect RNA comprising the same sequence as the specific sequence of GII type SRSV RNA in a single tube at a constant temperature and in a single step, thus facilitating its application for automation.

EXAMPLES

Figure 1:
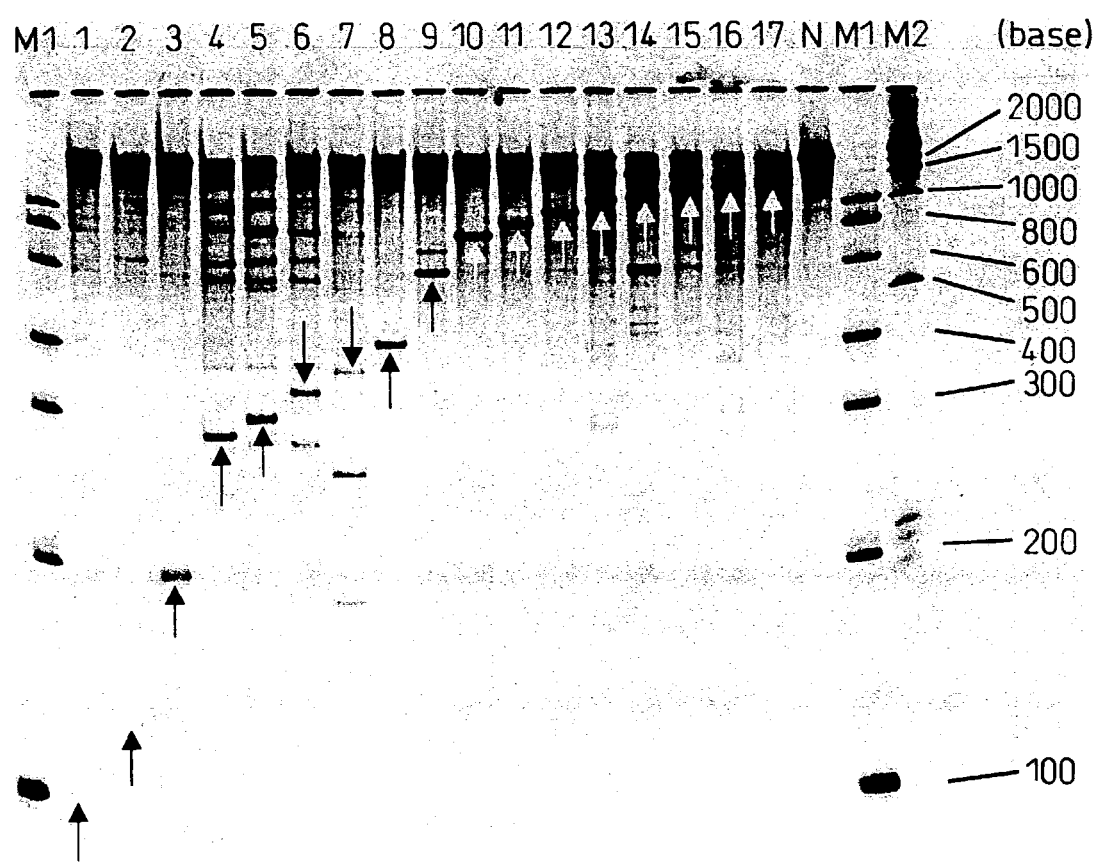
FIG. 1 is a urea modified 6% polyacrylamide electrophoresis diagram for samples after performing GII type SRSV standard RNA binding tests at 41° C., using oligonucleotides G2-1R to G2-17R (black and white inverted). The arrows indicate the positions of the specific bands. Lanes 1 to 17 show the results of the binding test using G2-1R to G2-17R respectively, and lane N represents the negative control (using only the diluent instead of RNA samples). The molecular weight markers (lanes M1 and M2) used therein are RNA markers (0.1 to 1 kb and 0.2 to 10 kb).

The present invention will now be explained in greater detail by way of examples, with the understanding that the invention is not limited by these examples.

Example 1

Specific binding of the oligonucleotides of the invention to GII type SRSV at 41° C. was examined.

(1) Of the GII type SRSV-RNA, a standard RNA (SEQ ID No. 10) comprising a region of 2843 bases in total containing the SEQ ID No. 1 region and a portion of the structural protein-coding gene region, as well as a 69 base-partial region derived from the 5' end of a vector (pCR2.1, Invitrogen) was quantified by ultraviolet absorption at 260 nm, and then diluted to a concentration of 0.62 pmol/μl with an RNA diluent (10 mM Tris-HCl (pH 8.0)), 0.1 mM EDTA, 1 mM DTT, 0.5 U/μl RNase Inhibitor (Takara Shuzo Co. Ltd.).

(2) 14 μl of a reaction solution having the following composition was dispensed into 0.5 ml volume PCR tubes (GENE AMP THIN-WALLED REACTION TUBE™, Perkin-Elmer Co. Ltd.)

Reaction Solution Composition (each concentration represents that in a final reaction solution volume of 15 μl)
  60 mM Tris-HCl buffer (pH 8.6)
  17 mM magnesium chloride
  90 mM potassium chloride
  39U RNase inhibitor
  1 mM DTT
  0.066 μM standard RNA
  0.2 μM oligonucleotide (one of the oligonucleotides shown below was used)
  G2-1R (Oligonucleotide complementary to base Nos.23 to 42 of SEQ ID No. 1; SEQ ID No. 2)
  G2-2R (Oligonucleotide complementary to base Nos.46 to 67 of SEQ ID No. 1; SEQ ID No. 3)
  G2-3R (Oligonucleotide complementary to base Nos.104 to 125 of SEQ ID No. 1; SEQ ID No. 4)
  G2-4R (Oligonucleotide complementary to base Nos.201 to 220 of SEQ ID No. 1; SEQ ID No. 11)
  G2-5R (Oligonucleotide complementary to base Nos.222 to 241 of SEQ ID No. 1; SEQ ID No. 12)
  G2-6R (Oligonucleotide complementary to base Nos.249 to 271 of SEQ ID No. 1; SEQ ID No. 13)
  G2-7R (Oligonucleotide complementary to base Nos.274 to 293 of SEQ ID No. 1; SEQ ID No. 14)
  G2-8R (Oligonucleotide complementary to base Nos.324 to 344 of SEQ ID No. 1; SEQ ID No. 5)
  G2-9R (Oligonucleotide complementary to base Nos.512 to 533 of SEQ ID No. 1; SEQ ID No. 15)
  G2-10R (Oligonucleotide complementary to base Nos.725 to 745 of SEQ ID No. 1; SEQ ID No. 6)
  G2-11R (Oligonucleotide complementary to base Nos.812 to 831 of SEQ ID No. 1; SEQ ID No. 7)
  G2-12R (Oligonucleotide complementary to base Nos.930 to 952 of SEQ ID No. 1; SEQ ID No. 8)
  G2-13R (Oligonucleotide complementary to base Nos.1061 to 1081 of SEQ ID No. 1; SEQ ID No. 16)
  G2-14R (Oligonucleotide complementary to base Nos.1107 to 1126 of SEQ ID No. 1; SEQ ID No. 17)
  G2-15R (Oligonucleotide complementary to base Nos.1222 to 1244 of SEQ ID No. 1; SEQ ID No. 18)
  G2-16R (oligonucleotide complementary to base Nos.1280 to 1299 of SEQ ID No. 1; SEQ ID No. 19)
  G2-17R (Oligonucleotide complementary to base Nos.1303 to 1322 of SEQ ID No. 1; SEQ ID No. 9)
  Distilled water for adjusting volume (3) The reaction solutions were then incubated at 41° C. for 5 minutes, and then 1 μl of 8 U/μl AMV-Reverse Transcriptase (Takara Shuzo Co. Ltd.; an enzyme which cleaves RNA of a double stranded-DNA/RNA) was added thereto.

(4) Subsequently, the PCR tubes were incubated at 41° C. for 10 minutes.

(5) Modified-urea polyacryalmide gel (acrylamide concentration: 6%; urea: 7M) electrophoresis was conducted to confirm the cleaved fragments after the reaction. Dyeing following the electrophoresis was carried out with SYBR GREEN II™(Takara Shuzo Co. Ltd.). Upon binding of the oligonucleotide to the specific site of the target RNA, RNA of the double stranded DNA/RNA is cleaved by the ribonuclease H activity of AMV-Reverse Transcriptase and, thereby, a characteristic band could be observed.

The results of the electrophoresis are shown in FIG. 1 (black and white inverted). If the oligonucleotide binds specifically to the standard RNA, the standard RNA will be decomposed at this region, yielding a decomposition product having a characteristic chain length. Specific bands were confirmed with G2-1R, G2-2R, G2-3R, G2-8R, G2-10R, G2-11R, G2-12R, G2-17R. This indicated that these oligonucleotides bind strongly to the GII type SRSV RNA under a certain condition at a temperature of 41° C. The numbers in Table 1 are assigned by designating the initiation base of SEQ ID No. 1 in the base sequence of SEQ. ID No. 10 as 1. The circles in the table indicate that a specific band was observed, and the symbols "X" indicate that a specific band was observed together with a non-specific band.

TABLE 1

| Oligo name | Position | Expected band length (base) | Result |
|---|---|---|---|
| G2-1R | 23 | 91, 2799 | ○ |
| G2-2R | 46 | 114, 2744 | ○ |
| G2-3R | 104 | 172, 2716 | ○ |
| G2-4R | 201 | 269, 2621 | X |
| G2-5R | 222 | 290, 2600 | X |
| G2-6R | 249 | 317, 2570 | X |
| G2-7R | 274 | 342, 2548 | X |
| G2-8R | 324 | 382, 2497 | ○ |
| G2-9R | 512 | 580, 2308 | X |
| G2-10R | 725 | 793, 2096 | ○ |

TABLE 1-continued

| Oligo name | Position | Expected band length (base) | Result |
|---|---|---|---|
| G2-11R | 812 | 880, 2010 | ○ |
| G2-12R | 930 | 998, 1889 | ○ |
| G2-13R | 1061 | 1129, 1760 | X |
| G2-14R | 1107 | 1175, 1715 | X |
| G2-15R | 1222 | 1290, 1597 | X |
| G2-16R | 1280 | 1348, 1542 | X |
| G2-17R | 1303 | 1371, 1519 | ○ |

Example 2

The specificities against GII type SRSV of the oligonucleotides selected in Example 1 were confirmed.

(1) As a GI type SRSV standard RNA, an RNA comprising base Nos.1 to 3861 of the structural gene of an RNA-dependent RNA polymerase derived from the base sequence of Chiba virus RNA was quantified by ultraviolet absorption at 260 nm, and then diluted with an RNA diluent (10 mM Tris-HCl (pH 8.0), 0.1 mM EDTA, 1 mM DTT, 0.5 U/µl RNase Inhibitor (Takara Shuzo Co. Ltd.)) to 0.45 pmol/µl.

(2) As a GII type SRSV standard RNA, the same RNA solution as in Example 1 (SEQ ID No. 10; concentration: 0.62 pmol/µl) was used.

(3) 14 µl of a reaction solution having the following composition was dispensed into 0.5 ml volume PCR tubes (GENE AMP THIN-WALLED REACTION TUBE™, Perkin-Elmer Co. Ltd.)

Reaction Solution Composition (each concentration represents that in a final reaction solution volume of 15 µl)
  60 mM Tris-HCl buffer (pH 8.6)
  17 mM magnesium chloride
  90 mM potassium chloride
  39U RNase inhibitor (Takara Shuzo Co. Ltd.)
  1 mM DTT
  0.066 µM standard RNA
  0.2 µM oligonucleotide (one of the oligonucleotides shown below was used)
    G2-1R (SEQ ID No. 2)
    G2-2R (SEQ ID No. 3)
    G2-3R (SEQ ID No. 4)
    G2-8R (SEQ ID No. 5)
    G2-10R (SEQ ID No. 6)
    G2-11R (SEQ ID No. 7)
    G2-12R (SEQ ID No. 8)
    G2-17R (SEQ ID No. 9)

(4) The above reaction solutions were then incubated at 41° C. for 5 minutes, and then 1 µl of 8 U/µl AMV-Reverse Transcriptase (Takara Shuzo Co. Ltd.) was added thereto.

(5) Subsequently, the PCR tubes were incubated at 41° C. for 10 minutes.

(6) Modified-urea polyacrylamide gel (aerylamide concentration: 6%; urea: 7M) electrophoresis was conducted to confirm the cleaved fragments after the reaction. Dyeing following the electrophoresis was carried out with SYBR GREEN II™ (Takara Shuzo Co. Ltd.). Upon binding of the oligonucleotide to the specific site of the target RNA, RNA of the double stranded DNA/RNA is cleaved by the ribonuclease H activity of AM V-Reverse Transcriptase and, thereby, a characteristic band could be observed.

Figure 2:
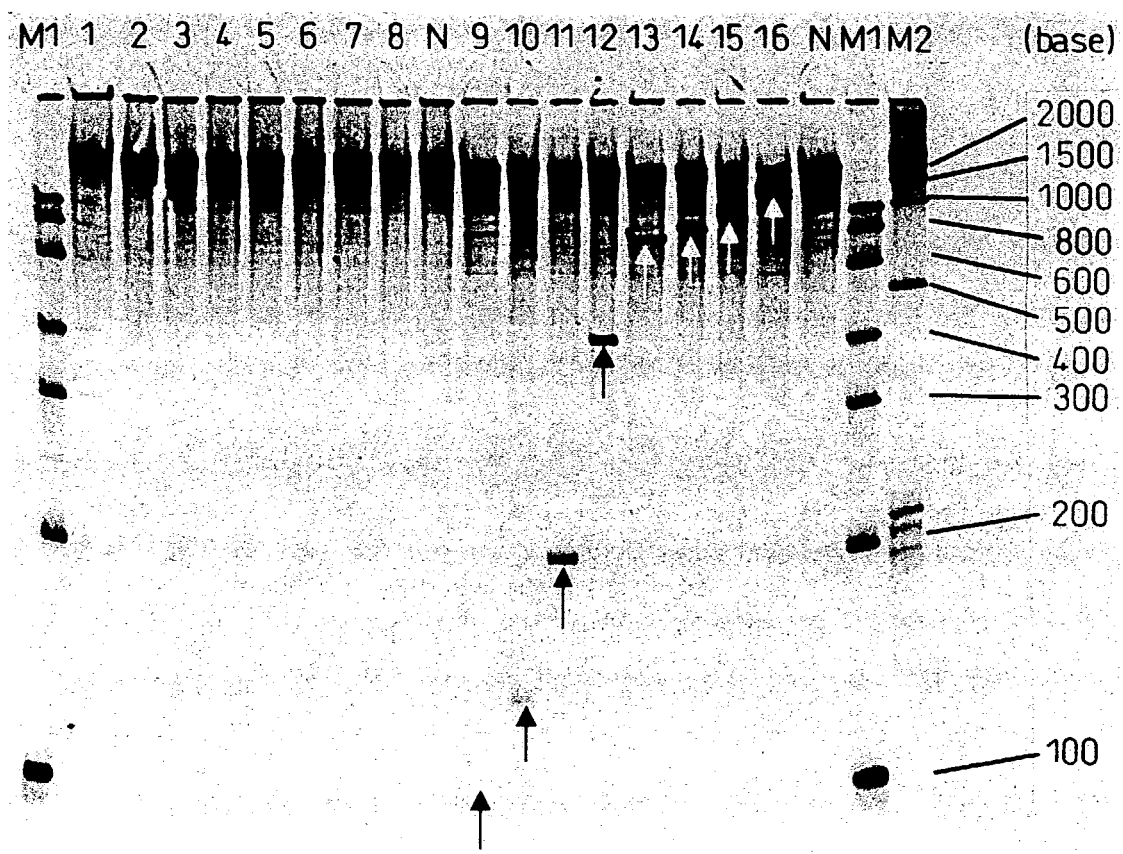
FIG. 2 is a urea modified 6% polyacrylamide electrophoresis diagram for samples after performing GII type SRSV standard RNA binding tests at 41° C., using the oligonucleotides selected in Example 1 (black and white inverted). The arrows indicate the positions of the specific bands. Lanes 1 to 8 show the results for GI type SRSV standard RNA of the binding tests, and lanes 9 to 16 show the results for GII type SRSV standard RNA of the binding test. Lanes 1 and 9, lanes 2 and 10, lanes 3 and 11, lanes 4 and 12, lanes 5 and 13, lanes 6 and 14, lanes 7 and 15, as well as lanes 8 and 16 used oligonucleotides G2-1R, G2-2R, G2-3R, G2-8R, G2-10R, G2-11R, G2-12R and G2-17R, respectively, and lane N represents the negative control (using only the diluent instead of RNA samples). The molecular weight markers (lanes M1 and M2) used therein are RNA markers (0.1 to 1 kb and 0.2 to 10 kb).

The results of the electrophoresis are shown in FIG. 2 (black and white inverted). If the oligonucleotide binds specifically to the standard RNA, the standard RNA will be decomposed at this region, yielding a decomposition product having a characteristic chain length. The results showed that the oligonucleotides selected in Example 1 bind specifically to GII type SRSV RNA.

As explained above, the oligonucleotides of the present invention are oligonucleotides that complementary bind to RNA derived from GII type SRSV, even under conditions of relatively low and constant temperature (35-50° C., preferably 41° C.), which tend to produce an intramolecular structure in RNA and prevent binding of primers or probes thereto. Specific binding of the oligonucleotides is therefore possible without heat denaturation of the target RNA. The oligonucleotides of the invention are thus useful as oligonucleotides for cleavage, amplification, detection or the like of RNA derived from GII type SRSV, i.e. as oligonucleotide primers or oligonucleotide probes to be used in RNA amplification methods.

Furthermore, the oligonucleotides of the invention are also useful for amplification and detection of GII type SRSV gene.

The oligonucleotides of the invention are not limited to the sequences shown in the Sequence Listings (20 to 23 mers), and may be oligonucleotides comprising at least 10 contiguous bases within those sequences. This is apparent from the fact that an order of 10-mer base sequence is sufficient to ensure adequate specificity of primers or probes to target nucleic acids under relatively low temperature condition (preferably, at 41° C.).

Example 3

RNA amplification reactions were carried out using the oligonucleotides which specifically bind to the RNA of GII type SRSV.

(1) Of the GII type SRSV-RNA, a standard RNA (SEQ ID No. 10) comprising a region of totally 2843 bases containing the entire RNA-dependent RNA polymerase gene region and a portion of the structural protein-coding gene region, as well as a 69 base-partial region derived from the 5' end of a vector (pCR 2.1, Invitrogen) was quantified by ultraviolet absorption at 260 nm, and then diluted to $1.0 \times 10^4$ mol/5 µl with an RNA diluent (10 mM Tris-HCl (pH 8.0), 1 mM EDTA, 0.5 U/µl RNase Inhibitor (Takara Shuzo Co. Ltd.), 5 mM DTT). In the control test sections (negative), only the diluent was used.

(2) 20.8 µl of a solution having the following composition was dispensed into 0.5 ml volume PCR tubes (GENE AMP THIN-WALLED REACTION TUBE™, Perkin-Elmer Co. Ltd.), followed by addition of 5 µl of the above RNA sample.

Reaction Solution Composition (each concentration represents that in a final reaction solution volume of 30 µl)
  60 mM Tris-HCl buffer (pH 8.6)
  17 mM magnesium chloride
  90 mM potassium chloride
  39U RNase inhibitor
  1 mM DTT
  0.25 µl of each dATP, dCTP, dGTP, dTTP
  3.6 mM ITP
  3.0 mM of each ATP, CTP, GTP, UTP
  0.16 µM first oligonucleotide
  1.0 µM second oligonucleotide
  1.0 µM third oligonucleotide
  13% DMSO
  Distilled water for adjusting volume (3) RNA amplification reactions were carried out using the oligonucleotides of the sequences listed in Table 2, as the first, second and third oligonucleotides. Solutions were prepared so that the combinations of the first, second and third oligonucleotides would be those as listed in Table 2.

(4) After incubating the above reaction solutions for 5 minutes at 41° C., 4.2 µl of an enzyme liquid having the following composition was added.

Composition of Enzyme Solution (each figure represents the amount in a final reaction solution volume of 30 µl)
   1.7% sorbitol
   3 µg bovine serum albumin
   142U T7 RNA polymerase (Gibco)
   8U AMV-Reverse Transcriptase
   (Takara Shuzo Co. Ltd.)
   Distilled water for adjusting volume (5) Subsequently, the PCR tubes were incubated at 41° C. for 30 minutes.

(6) In order to identify the RNA amplified portion after the reaction, agarose gel (agarose concentration 4%) electrophoresis was performed. Dyeing following the electrophoresis was performed with SYBR GREEN II™(Takara Shuzo Co. Ltd.). When an oligonucleotide probe binds to the specific portion of the target RNA, the RNA portion between the second and third oligonucleotide is amplified, thereby a characteristic band could be observed.

Figure 3:
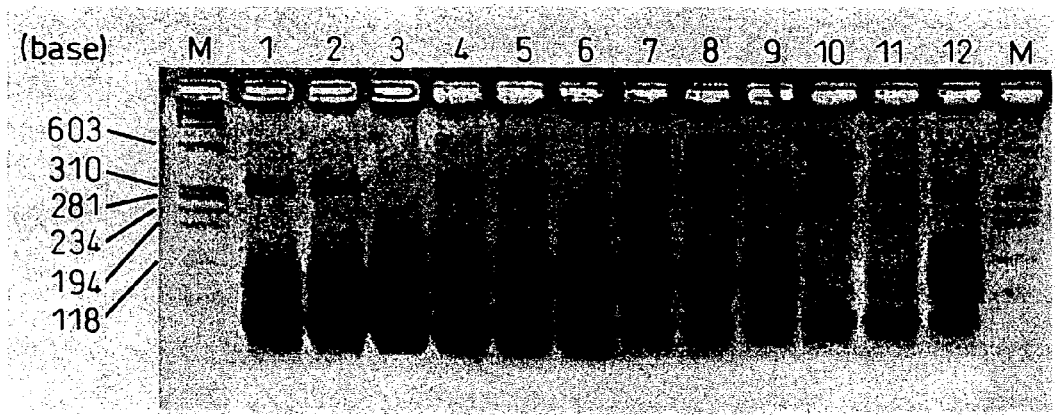
FIG. 3 is an electrophoresis diagram for RNA amplification reactions in Example 3 using oligonucleotide combinations (a) to (d) shown in Table 2 (black and white inverted), with an initial RNA amount of $10^4$ copies/test. Lanes 1 and 2 are the results for combination (a), lanes 4 and 5 are for combination (b), lanes 7 and 8 are for combination (c), lanes 10 and 11 are for combination (d), while lanes 3, 6, 9, and 12 are for the negative control (using only the diluent instead of RNA samples). The molecular marker used therein was φX174/Hae III digest (Marker 4). Specific bands were confirmed in every combination.
Figure 4:
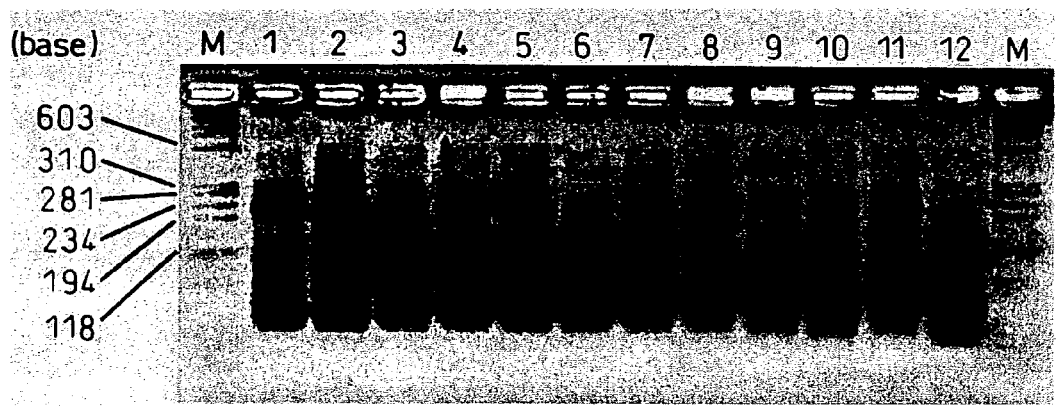
FIG. 4 is an electrophoresis diagram for RNA amplification reactions in Example 3 using oligonucleotide combinations (e) to (h) shown in Table 2 (black and white inverted), with an initial RNA amount of $10^4$ copies/test. Lanes 1 and 2 are the results for combination (e), lanes 4 and 5 are for combination (f), lanes 7 and 8 are for combination (g), lanes 10 and 11 are for combination (h), while lanes 3, 6, 9, and 12 are for the negative control (using only the diluent instead of RNA samples). The molecular marker used therein was φX174/Hae III digest (Marker 4). Specific bands were confirmed in every combination.
Figure 5:
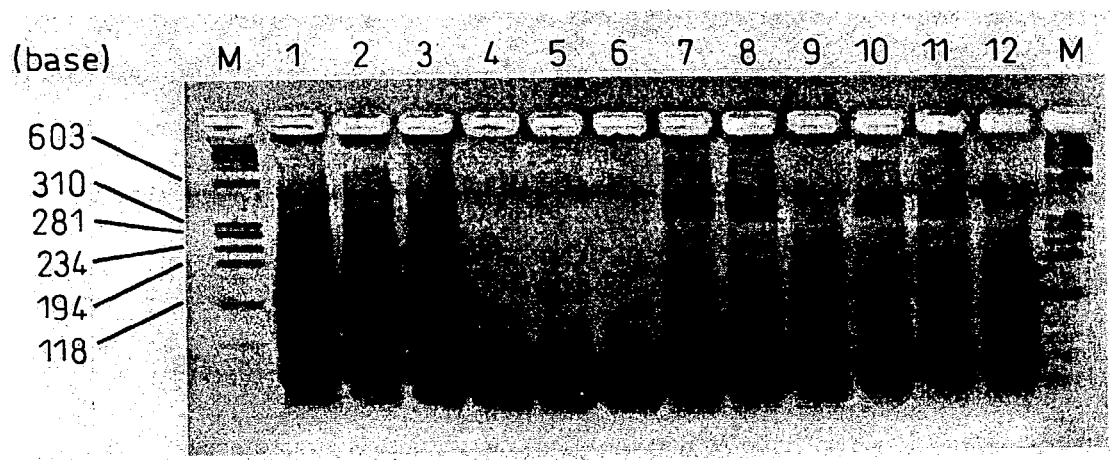
FIG. 5 is an electrophoresis diagram for RNA amplification reactions in Example 3 using oligonucleotide combinations (i) to (l) shown in Table 2 (black and white inverted), with an initial RNA amount of $10^4$ copies/test. Lanes 1 and 2 are the results for combination (i), lanes 4 and 5 are for combination (j), lanes 7 and 8 are for combination (k), lanes 10 and 11 are for combination (l), while lanes 3, 6, 9, and 12 are for the negative control (using only the diluent instead of RNA samples). The molecular marker used therein was φX174/Hae III digest (Marker 4). Of these combinations, specific bands were confirmed in combinations (k) and (l).

The results of the electrophoresis are shown in FIGS. 3 to 5 (black and white inverted). The chain lengths of the specific bands amplified in this reaction are shown in Table 2. Since specific bands were confirmed in combinations from (a) to (h), and from (k) to (l), it was demonstrated that the oligonucleotides used in these combinations are effective in detecting GII type SRSV.

TABLE 2

| Combination | 1st Oligo | 2nd Oligo | 3rd Oligo | Amplification produced chain length (no. of bases) |
|---|---|---|---|---|
| (a) | G2-1S | G2-1F1 | G2-8R | 314 |
| (b) | G2-1S | G2-1F2 | G2-8R | 317 |
| (c) | G2-2S | G2-2F1 | G2-8R | 289 |
| (d) | G2-2S | G2-2F2 | G2-8R | 292 |
| (e) | G2-3S | G2-3F1 | G2-8R | 231 |
| (f) | G2-3S | G2-3F2 | G2-8R | 234 |
| (g) | G2-10S | G2-10F1 | G2-12R | 219 |
| (h) | G2-10S | G2-10F2 | G2-12R | 222 |
| (i) | G2-11S | G2-11F1 | G2-12R | 133 |
| (j) | G2-11S | G2-11F2 | G2-12R | 136 |
| (k) | G2-12S | G2-12F1 | G2-17R | 382 |
| (l) | G2-12s | G2-12F2 | G2-17R | 385 |

Table 2 shows the combinations of first, second and third oligonucleotides used in this example, as well as the chain lengths of the amplified specific bands resulted from the RNA amplification reaction using these combinations. The 3' end hydroxyl group of each first oligonucleotide base sequence was aminated. In each second oligonucleotide base sequence, the region of the 1st "A" to the 22nd "A" from the 5' end corresponds to the T7 promoter region, and the subsequent region from the 23rd "G" to the 28th "A" corresponds to the enhancer sequence. The base numbers are assigned by designating the initiation base of the RNA-dependent RNA polymerase gene of GII SRSV in SEQ ID No. 36 as 1.

First oligonucleotide
   G2-1S (SEQ ID No. 36, base Nos.4 to 42)
   G2-2S (SEQ ID No. 37, base Nos.29 to 67)
   G2-3S (SEQ ID No. 38, base Nos.87 to 125)
   G2-10S (SEQ ID No. 39, base Nos.707 to 745)
   G2-11S (SEQ ID No. 40, base Nos.792 to 831)
   G2-12S (SEQ ID No. 41, base Nos.1303 to 1322)

Second oligonucleotide
   G2-1F1 (SEQ ID No. 42, base Nos.37 to 59)
   G2-1F2 (SEQ ID No. 43, base Nos.34 to 56)
   G2-2F1 (SEQ ID No. 44, base Nos.62 to 84)
   G2-2F2 (SEQ ID No. 45, base Nos.59 to 81)
   G2-3F1 (SEQ ID No. 46, base Nos.120 to 142)
   G2-3F2 (SEQ ID No. 47, base Nos.117 to 139)
   G2-10F1 (SEQ ID No. 48, base Nos.740 to 762)
   G2-10F2 (SEQ ID No. 49, base Nos.737 to 759)
   G2-11F1 (SEQ ID No. 50, base Nos.826 to 848)
   G2-11F2 (SEQ ID No. 51, base Nos.823 to 845)
   G2-12F1 (SEQ ID No. 52, base Nos.947 to 969)
   G2-12F2 (SEQ ID No. 53, base Nos.944 to 966)

Third oligonucleotide
   G2-8R (SEQ ID No. 28, base Nos.324 to 344)
   G2-12R (SEQ ID No. 30, base Nos.930 to 952)
   G2-17R (SEQ ID No. 31, base Nos.1303 to 1322)

Example 4

Combinations of oligonucleotide primers according to the present invention were used for specific detection of different initial copy numbers of the target GII type SRSV RNA.

(1) The same GI type SRSV standard RNA (SEQ ID No. 10) as used in Example 3 was diluted with an RNA diluent (10 mM Tris-HCl (pH 8.0), 1 mM EDTA, 0.5 U/µl RNase Inhibitor (Takara Shuzo Co. Ltd.), 5 mM DTT,) to concentrations ranging from $1.0 \times 10^5$ copies/5 µl to $10^1$ copies/5 µl. In the control testing sections, only the diluent was used (Negative).

(2) 20.8 µl of a reaction solution having the composition shown below was dispensed into 0.5 ml volume PCR tubes (GENE AMP THIN-WALLED REACTION TUBE™, Perkin-Elmer Co. Ltd.) followed by addition of 5 µl of the above RNA sample.

Reaction Solution Composition (each concentration represents that in a final reaction solution of 30 µl)
   60 mM Tris-HCl buffer (pH 8.6)
   17 mM magnesium chloride
   150 mM potassium chloride
   39U RNase Inhibitor
   1 mM DTT
   0.25 mM each of dATP, dCTP, dGTP and dTTP
   3.6 mM ITP
   3.0 mM each of ATP, CTP, GTP and UTP
   0.16 µM first oligonucleotide (G2-1S, SEQ ID No. 36, wherein its 3' end is aminated)
   1.0 µM second oligonucleotide (G2-1F2, SEQ ID No. 43)
   1.0 µM third oligonucleotide (G2-8R, SEQ ID No. 28)
   25 nM intercalator fluorescent pigment-labeled oligonucleotide (YO-G2 SRSV-S-G, SEQ ID No. 35, labeled with an intercalator fluorescent pigment at the phosphorous atom between the 7th "T" and the 8th "A" from the 5' end, and modified with a glycol group at its 3' end hydroxyl)
   13% DMSO
   Distilled water for adjusting volume (3) After incubating the above reaction solution for 5 minutes at 41° C., 4.2 µl of an enzyme solution having the following composition and pre-incubated for 2 minutes at 41° C. was added.

Enzyme Solution Composition (each concentration represents that in a final reaction solution of 30 µl)
   1.7% sorbitol
   3 µg bovine serum albumin
   142U T7 RNA polymerase (Gibco)
   8U AMV-Reverse Transcriptase (Takara Shuzo Co. Ltd.)

Distilled water for adjusting volume (4) The PCR tube was then incubated at 41° C. using a direct-measurable fluorescence spectrophotometer equipped with a temperature-controller, and the reaction solution was periodic measured at an excitation wavelength of 470 nm and a fluorescent wavelength of 510 nm.

FIG. 6(A) shows the time-course changes in the fluorescence increase ratio (fluorescence intensity at predetermined time/background fluorescence intensity) of the sample, where enzyme was added at 0 minutes. FIG. 6(B) shows the relationship between the logarithm of the initial RNA amount and the rise time (time at which the relative fluorescence reaches the negative sample's average value plus 3 standard deviations; i.e., the time to reach 1.2). The initial RNA amount was between $10^1$ copies/test and $10^5$ copies/test.

Figure 6:
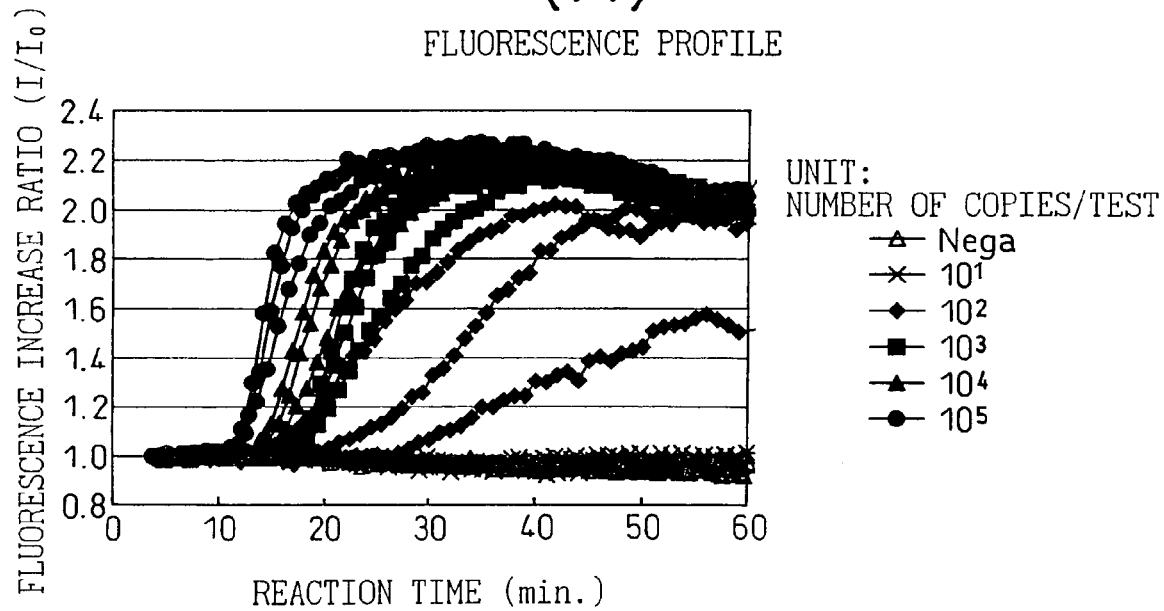
FIG. 6 shows a graph (A) of the fluorescence increase ratio which increases as the reaction time and production of RNA progress, and a calibration curve (B) obtained for the initial RNA amount logarithm and the rising time, with an initial RNA amount of between $10^1$ copies/test and $10^5$ copies/test in Example 4. The initial amount of $10^3$ copies/test of RNA was detectable after approximately 20 minutes of reaction, and a correlation between initial RNA amount and rise time was demonstrated.
Figure 6:
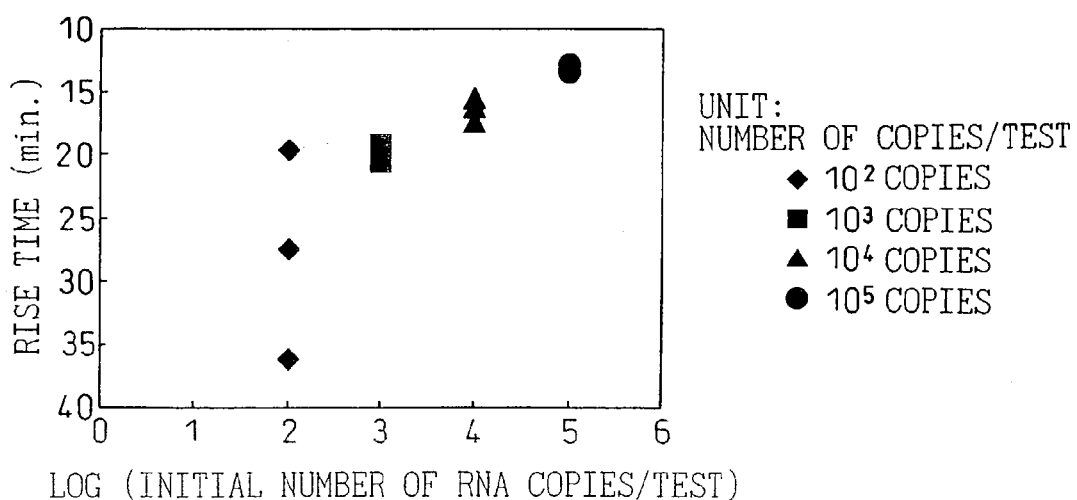

FIG. 6 shows that $10^3$ copies were detected after approximately 20 minutes. A fluorescent profile and calibration curve depending on the initial concentration of the labeled RNA were obtained, indicating that it is possible to quantify the GII type SRSV RNA present in unknown samples. This demonstrated that rapid, highly sensitive detection of GII type SRSV RNA is possible by this method.

As explained above, the present invention provides useful combinations of oligonucleotide primers or oligonucleotide probes which specifically bind to RNA derived from GII type SRSV, and rapidly amplify and detect the target RNA, even under relatively low and constant temperature (35-50° C. and preferably 41° C.) conditions in which an RNA in a sample would form an intramolecular structure which inhibit the primer and probe binding.

The base lengths of the oligonucleotides in the combinations of the present invention are not limited to the ones concretely described herein, and the present oligonucleotides may include those comprised of at least 10 contiguous bases within these sequences. This is apparent from the fact that about 10-mer base sequence is sufficient to ensure adequate specificity of primers or probes to target nucleic acids under relatively low temperature condition (preferably, at 41° C.).

What is claimed is:

1. An isolated polynucleotide comprising SEQ ID NO:1 or the complementary sequence to SEQ ID NO:1.

2. A composition comprising the isolated polynucleotide of claim 1 and a carrier.

3. The isolated polynucleotide of claim 1, comprising SEQ ID NO:1.

4. A composition comprising the isolated polynucleotide of claim 3 and a carrier.

5. The isolated polynucleotide of claim 1, comprising the complementary sequence to SEQ ID NO:1.

6. A composition comprising the isolated polynucleotide of claim 5 and a carrier.

* * * * *

SEQUENCE LISTING

<160> NUMBER OF SEQ ID NOS: 53

<210> SEQ ID NO 1
<211> LENGTH: 1530
<212> TYPE: DNA
<213> ORGANISM: Human calicivirus

<400> SEQUENCE: 1

```
ggcggtgaca ataagggaac ctactgtggt gcaccaatct taggtccagg cagtgcccca      60
aaactcagca ccaagactaa attttggaga tcatccacag caccactccc acctggtacc     120
tatgaaccag cctaccttgg cggcaaggac cccagagtca agggtggtcc ttcattgcaa     180
caagttatga gggaccagct gaaaccattc actgaaccca ggggtaaacc accaaaacca     240
agtgtgttag aagctgccaa gaaaaccatc atcaatgtcc ttgaacaaac aattgatcca     300
cctcaaaagt ggtcattcgc gcaagcatgc gcatccctcg acaagaccac ctctagtggt     360
cacccgcatc acatgcggaa aaatgactgc tggaacgggg agtccttcac aggcaaattg     420
gcagaccagg cttccaaggc caacctgatg tacgaagagg gaaagaacat gaccccagtt     480 tacacggggtg cgcttaagga cgagctggtc aagactgaca aaatttatgg caaaatcaaa     540
aagaggcttc tctggggctc ggacctggcg accatgatcc ggtgcgctcg ggcttttggg     600
ggcctgatgg atgaattcaa ggcacattgt gtcacactcc ccgtcagagt gggtatgaat     660
atgaatgagg atggtcctat catctttgag agacactcca gatataaata tcactatgat     720
gctgattact ctcggtggga ctcaacacaa cagagggccg tattagcagc agccttagaa     780
atcatggtta agttctcccc agaacctcat ctggcccaaa aggttgcaga agaccttctc     840
tctcccagcg tgatggatgt aggtgacttc agaatatcaa tcaatgaggg tctcccctcc     900
ggggtaccct gcacctccca atggaactcc atcgcccact ggctcctcac tctctgtgca     960
ctttctgagg ttacaaacct gtcccctgac attatccagg ccaactccct cttttccttc    1020
tatggtgatg atgaaattgt gagcacagac gtaaagctgg acccagagaa gttgacagca    1080
aaactcaagg aatacgggct gaaaccaacc cgccctgaca agactgaggg acccettgtt    1140 atctctgagg acctgaatgg cttgacctte ctgcggagga ctgtgacccg cgatccagct    1200
ggctggtttg gaaaattgga acagagttca atacttaggc aaatgtactg gactaggggc    1260
```

-continued

```
cctaatcatg aagacccatc tgaaacaatg ataccacact cccaaagacc catacaatta      1320
atgtctttgc tgggcgaggc tgccctccac ggcccagcat tctacagcaa aatcagcaag      1380
ttggtcattg cagaactaaa ggaaggtggc atggatttct acgtgcccag acaagagcca      1440
atgttcagat ggatgagatt ctcagatctg agcacgtggg agggcgatcg caatctggct      1500
cccagttttg tgaatgaaga tggcgtcgaa                                       1530
```

<210> SEQ ID NO 2
<211> LENGTH: 20
<212> TYPE: DNA
<213> ORGANISM: Artificial Sequence
<220> FEATURE:
<223> OTHER INFORMATION: synthetic DNA

<400> SEQUENCE: 2
taagattggt gcaccacagt                                                  20

<210> SEQ ID NO 3
<211> LENGTH: 22
<212> TYPE: DNA
<213> ORGANISM: Artificial Sequence
<220> FEATURE:
<223> OTHER INFORMATION: synthetic DNA

<400> SEQUENCE: 3
tgagttttgg ggcactgcct gg                                               22

<210> SEQ ID NO 4
<211> LENGTH: 22
<212> TYPE: DNA
<213> ORGANISM: Artificial Sequence
<220> FEATURE:
<223> OTHER INFORMATION: synthetic DNA

<400> SEQUENCE: 4
tcataggtac caggtgggag tg                                               22

<210> SEQ ID NO 5
<211> LENGTH: 21
<212> TYPE: DNA
<213> ORGANISM: Artificial Sequence
<220> FEATURE:
<223> OTHER INFORMATION: synthetic DNA

<400> SEQUENCE: 5
ttgtcgaggg atgcgcatgc t                                                21

<210> SEQ ID NO 6
<211> LENGTH: 21
<212> TYPE: DNA
<213> ORGANISM: Artificial Sequence
<220> FEATURE:
<223> OTHER INFORMATION: synthetic DNA

<400> SEQUENCE: 6
ttgagtccca ccgagagtaa t                                                21

<210> SEQ ID NO 7
<211> LENGTH: 20
<212> TYPE: DNA
<213> ORGANISM: Artificial Sequence
<220> FEATURE:
<223> OTHER INFORMATION: synthetic DNA

<400> SEQUENCE: 7
ttctgcaacc ttttgggcca                                                    20

<210> SEQ ID NO 8
<211> LENGTH: 23
<212> TYPE: DNA
<213> ORGANISM: Artificial Sequence
<220> FEATURE:
<223> OTHER INFORMATION: synthetic DNA

<400> SEQUENCE: 8
gagtgaggag ccagtgggcg atg                                                23

<210> SEQ ID NO 9
<211> LENGTH: 20
<212> TYPE: DNA
<213> ORGANISM: Artificial Sequence
<220> FEATURE:
<223> OTHER INFORMATION: synthetic DNA

<400> SEQUENCE: 9
attaattgta tgggtctttg                                                    20

<210> SEQ ID NO 10
<211> LENGTH: 2910
<212> TYPE: RNA
<213> ORGANISM: Human calicivirus

<400> SEQUENCE: 10
gcgaauuggg cccucuagau gcaugcucga gcggccgcca gugugaugga uaucugcaga 60
auucggcuug gcggugacaa uaagggaacc uacugugggug caccaaucuu agguccaggc 120
agugccccaa aacucagcac caagacuaaa uuuuggagau cauccacagc accacuccca 180
ccugguaccu augaaccagc cuaccuuggc ggcaaggacc ccagagucaa ggguggucuu 240
ucauugcaac aaguuaugag ggaccagcug aaaccauuca cugaacccag ggguaaacca 300
ccaaaaccaa gugugguuaga agcugccaag aaaaccauca ucaauguccu ugaacaaaca 360
auugauccac cucaaaagug gucauucgcg caagcaugcg caucccucga caagaccacc 420
ucuagugguc acccgcauca caugcggaaa aaugacugcu ggaacgggga guccuucaca 480
ggcaaauugg cagaccaggc uuccaaggcc aaccugaugu acgaagaggg aaagaacaug 540
accccaguuu acacgggugc gcuuaaggac gagcugguca agacugacaa aauuuauggc 600
aaaaucaaaa agaggcuucu cuggggcucg gaccuggcga ccaugauccg gugcgcucgg 660
gcuuuugggg gccugaugga ugaauucaag gcacauugug ucacacuccc cgucagagug 720
gguaugaaua ugaaugagga ugguccuauc aucuuugaga gacacuccag auauaaauau 780
cacuaugaug cugauuacuc ucggugggac ucaacacaac agagggccgu auuagcagca 840
gccuuagaaa ucaugguuaa guucuccccca gaaccucauc uggcccaaaa gguugcagaa 900
gaccuucucu cucccagcgu gauggaugua ggugacuuca gaauaucaau caaugagggu 960
cuccccuccg gguacccug caccucccaa uggaacucca ucgcccacug gcuccucacu 1020
cucugugcac uuucugaggu uacaaaccug uccccugaca uuauccaggc caacucccuc 1080
uuuuccuucu augugauga ugaaauugug agcacagacg uaaagcugga cccagagaag 1140
uugacagcaa aacucaagga auacgggcug aaaccaaccc gcccugacaa gacugaggga 1200
ccccuuguua ucucugagga ccugaauggc uugaccuucc ugcggaggac ugugacccgc 1260
gauccagcug gcugguuugg aaaauuggaa cagaguucaa uacuuaggca aauguacugg 1320

-continued

```
acuagggcc cuaaucauga agacccaucu gaaacaauga uaccacacuc ccaaagaccc    1380
auacaauuaa ugucuuugcu gggcgaggcu gcccuccacg gcccagcauu cuacagcaaa    1440
aucagcaagu uggucauugc agaacuaaag gaagguggca uggauuucua cgugcccaga    1500
caagagccaa uguucagaug gaugagauuc ucagaucuga gcacguggga gggcgaucgc    1560
aaucuggcuc ccaguuuugu gaaugaagau ggcgucgaau gacgccgcuc caucaaauga    1620
uggugcagcu agucucguac cagagggcau uaaugagacu augccauugg aacccguugc    1680
uggcgcaucu auugcugccc cagugggcgg acaaaccaac auaauugacc ccuggauaag    1740
aacaaauuuu guacaagccc ccaauggaga guuuacagug ucaccaagaa auuccccugg    1800
agaaauuuua uuaaauuuag aauuaggacc agaucugaau ccuuauuugg cccaucuuuc    1860
aagaauguac aauggcuuau cuggaggugu ugaggugcaa gugucccuug cugggaacgc    1920
guucacagca gguaagauau uguuugcagc aaucccaccu aacuuuccug uagauaugau    1980
uagcccagcu caaauuacua ugcuucccca uuugauugua gauguuagga cuuuggaacc    2040
uauuaugaua cccuugccug auguuaggaa uguuucuau cauuuuaaua aucaaccuca    2100
accuagaaug agguuagggg cuaugcucua caccccauug aggucuaaug guucaggaga    2160
ugaugucuuc acugugucuu guagaguacu aacuaggcca acuccugauu ugaauuuau    2220 uuaccuggug cccccuucug uagaguccaa aacuaaacca uucacacuac caauauuaac    2280
cauuucugaa uugaccaacu cccgguuccc cauuccaauc gagcaauugu auacggcucc    2340
aaaugaaacc aauguugucc agugucagaa uggcaggugc accuagaug gagagcucca    2400 gggcacaacc cagcuguuau caagugcagu uugcucuuac aggggcagga cuguggcuaa    2460 uaaugggau aauugggacc aaaauuugcu ccagcugacc uauccaaaug ugcaagcua    2520 ugaccccacu gaugaagugc cagcaccauu gggcacucag gauuuuagug gauguugua    2580 uggaguguug acccaggaca auguugaaugu gagcacagga gaggccaaaa augcuaaggg    2640
aauauacaua uccaccacua guggaaaauu caccccaaaa auugggucaa uggauugca    2700 uucaauaacu gagcaugugc accccaacca acagucgcgg uucacccccg ucggagcgc    2760 cgugaaugag aacacccccu uccagcaaug gguucugcca cauuaugcag guagucucgc    2820
ucucaacacc aauuuggcac cugcuguugc cccgacuuuc ccuggugagc aauugcuguu    2880
cuucaggucc cgugucccau gcguucaagg                                    2910
```

<210> SEQ ID NO 11
<211> LENGTH: 20
<212> TYPE: DNA
<213> ORGANISM: Artificial Sequence
<220> FEATURE:
<223> OTHER INFORMATION: synthetic DNA

<400> SEQUENCE: 11
tgggttcagt gaatggtttc                                                20

<210> SEQ ID NO 12
<211> LENGTH: 20
<212> TYPE: DNA
<213> ORGANISM: Artificial Sequence
<220> FEATURE:
<223> OTHER INFORMATION: synthetic DNA

<400> SEQUENCE: 12
ttggttttgg tggtttaccc                                                20

<210> SEQ ID NO 13
<211> LENGTH: 23
<212> TYPE: DNA
<213> ORGANISM: Artificial Sequence
<220> FEATURE:
<223> OTHER INFORMATION: synthetic DNA

<400> SEQUENCE: 13
tgatggtttt cttggcagct tct                                    23

<210> SEQ ID NO 14
<211> LENGTH: 20
<212> TYPE: DNA
<213> ORGANISM: Artificial Sequence
<220> FEATURE:
<223> OTHER INFORMATION: synthetic DNA

<400> SEQUENCE: 14
attgtttgtt caaggacatt                                        20

<210> SEQ ID NO 15
<211> LENGTH: 22
<212> TYPE: DNA
<213> ORGANISM: Artificial Sequence
<220> FEATURE:
<223> OTHER INFORMATION: synthetic DNA

<400> SEQUENCE: 15
tttgccataa ttttgtcagt ct                                     22

<210> SEQ ID NO 16
<211> LENGTH: 21
<212> TYPE: DNA
<213> ORGANISM: Artificial Sequence
<220> FEATURE:
<223> OTHER INFORMATION: synthetic DNA

<400> SEQUENCE: 16
ttgctgtcaa cttctctggg t                                      21

<210> SEQ ID NO 17
<211> LENGTH: 20
<212> TYPE: DNA
<213> ORGANISM: Artificial Sequence
<220> FEATURE:
<223> OTHER INFORMATION: synthetic DNA

<400> SEQUENCE: 17
cagtcttgtc agggcgggtt                                        20

<210> SEQ ID NO 18
<211> LENGTH: 23
<212> TYPE: DNA
<213> ORGANISM: Artificial Sequence
<220> FEATURE:
<223> OTHER INFORMATION: synthetic DNA

<400> SEQUENCE: 18
atttgcctaa gtattgaact ctg                                    23

<210> SEQ ID NO 19
<211> LENGTH: 20
<212> TYPE: DNA
<213> ORGANISM: Artificial Sequence
<220> FEATURE:
<223> OTHER INFORMATION: synthetic DNA

```
<400> SEQUENCE: 19
gtgtggtatc attgtttcag                                              20

<210> SEQ ID NO 20
<211> LENGTH: 26
<212> TYPE: DNA
<213> ORGANISM: Artificial sequence
<220> FEATURE:
<223> OTHER INFORMATION: synthetic DNA

<400> SEQUENCE: 20
ccaatcttag gtccaggcag tgcccc                                       26

<210> SEQ ID NO 21
<211> LENGTH: 26
<212> TYPE: DNA
<213> ORGANISM: Artificial sequence
<220> FEATURE:
<223> OTHER INFORMATION: synthetic DNA

<400> SEQUENCE: 21
caaaactcag caccaagact aaattt                                       26

<210> SEQ ID NO 22
<211> LENGTH: 26
<212> TYPE: DNA
<213> ORGANISM: Artificial sequence
<220> FEATURE:
<223> OTHER INFORMATION: synthetic DNA

<400> SEQUENCE: 22
tacctatgaa ccagcctacc ttggcg                                       26

<210> SEQ ID NO 23
<211> LENGTH: 26
<212> TYPE: DNA
<213> ORGANISM: Artificial sequence
<220> FEATURE:
<223> OTHER INFORMATION: synthetic DNA

<400> SEQUENCE: 23
gggactcaac acaacagagg gccgta                                       26

<210> SEQ ID NO 24
<211> LENGTH: 26
<212> TYPE: DNA
<213> ORGANISM: Artificial sequence
<220> FEATURE:
<223> OTHER INFORMATION: synthetic DNA

<400> SEQUENCE: 24
tcctcactct ctgtgcactt tctgag                                       26

<210> SEQ ID NO 25
<211> LENGTH: 20
<212> TYPE: DNA
<213> ORGANISM: Artificial sequence
<220> FEATURE:
<223> OTHER INFORMATION: synthetic DNA

<400> SEQUENCE: 25
taagattggt gcaccacagt                                              20

<210> SEQ ID NO 26
```

```
<211> LENGTH: 22
<212> TYPE: DNA
<213> ORGANISM: Artificial sequence
<220> FEATURE:
<223> OTHER INFORMATION: synthetic DNA

<400> SEQUENCE: 26
tgagttttgg ggcactgcct gg                                              22

<210> SEQ ID NO 27
<211> LENGTH: 22
<212> TYPE: DNA
<213> ORGANISM: Artificial sequence
<220> FEATURE:
<223> OTHER INFORMATION: synthetic DNA

<400> SEQUENCE: 27
tcataggtac caggtgggag tg                                              22

<210> SEQ ID NO 28
<211> LENGTH: 21
<212> TYPE: DNA
<213> ORGANISM: Artificial sequence
<220> FEATURE:
<223> OTHER INFORMATION: synthetic DNA

<400> SEQUENCE: 28
ttgtcgaggg atgcgcatgc t                                               21

<210> SEQ ID NO 29
<211> LENGTH: 21
<212> TYPE: DNA
<213> ORGANISM: Artificial sequence
<220> FEATURE:
<223> OTHER INFORMATION: synthetic DNA

<400> SEQUENCE: 29
ttgagtccca ccgagagtaa t                                               21

<210> SEQ ID NO 30
<211> LENGTH: 23
<212> TYPE: DNA
<213> ORGANISM: Artificial sequence
<220> FEATURE:
<223> OTHER INFORMATION: synthetic DNA

<400> SEQUENCE: 30
gagtgaggag ccagtgggcg atg                                             23

<210> SEQ ID NO 31
<211> LENGTH: 20
<212> TYPE: DNA
<213> ORGANISM: Artificial sequence
<220> FEATURE:
<223> OTHER INFORMATION: synthetic DNA

<400> SEQUENCE: 31
attaattgta tgggtctttg                                                 20

<210> SEQ ID NO 32
<211> LENGTH: 20
<212> TYPE: DNA
<213> ORGANISM: Artificial sequence
<220> FEATURE:
<223> OTHER INFORMATION: synthetic DNA

<400> SEQUENCE: 32
```
agtggtgctg tggatgatct                                              20

<210> SEQ ID NO 33
<211> LENGTH: 20
<212> TYPE: DNA
<213> ORGANISM: Artificial sequence
<220> FEATURE:
<223> OTHER INFORMATION: synthetic DNA

<400> SEQUENCE: 33
ggacattgat gatggttttc                                              20

<210> SEQ ID NO 34
<211> LENGTH: 20
<212> TYPE: DNA
<213> ORGANISM: Artificial sequence
<220> FEATURE:
<223> OTHER INFORMATION: synthetic DNA

<400> SEQUENCE: 34
aattgtttgt tcaaggacat                                              20

<210> SEQ ID NO 35
<211> LENGTH: 20
<212> TYPE: DNA
<213> ORGANISM: Artificial sequence
<220> FEATURE:
<223> OTHER INFORMATION: synthetic DNA

<400> SEQUENCE: 35
ccaaggtagg ctggttcata                                              20

<210> SEQ ID NO 36
<211> LENGTH: 39
<212> TYPE: DNA
<213> ORGANISM: Artificial sequence
<220> FEATURE:
<223> OTHER INFORMATION: synthetic DNA

<400> SEQUENCE: 36
taagattggt gcaccacagt aggttccctt attgtcacc                         39

<210> SEQ ID NO 37
<211> LENGTH: 39
<212> TYPE: DNA
<213> ORGANISM: Artificial sequence
<220> FEATURE:
<223> OTHER INFORMATION: synthetic DNA

<400> SEQUENCE: 37
tgagttttgg ggcactgcct ggacctaaga ttggtgcac                         39

<210> SEQ ID NO 38
<211> LENGTH: 39
<212> TYPE: DNA
<213> ORGANISM: Artificial sequence
<220> FEATURE:
<223> OTHER INFORMATION: synthetic DNA

<400> SEQUENCE: 38
tcataggtac caggtgggag tggtgctgtg gatgatctc                         39

<210> SEQ ID NO 39
<211> LENGTH: 39
<212> TYPE: DNA

```
<213> ORGANISM: Artificial sequence
<220> FEATURE:
<223> OTHER INFORMATION: synthetic DNA

<400> SEQUENCE: 39
ttgagtccca ccgagagtaa tcagcatcat agtgatatt                              39

<210> SEQ ID NO 40
<211> LENGTH: 39
<212> TYPE: DNA
<213> ORGANISM: Artificial sequence
<220> FEATURE:
<223> OTHER INFORMATION: synthetic DNA

<400> SEQUENCE: 40
ttctgcaacc ttttgggcca gatgaggttc tggggagaa                              39

<210> SEQ ID NO 41
<211> LENGTH: 39
<212> TYPE: DNA
<213> ORGANISM: Artificial sequence
<220> FEATURE:
<223> OTHER INFORMATION: synthetic DNA

<400> SEQUENCE: 41
gagtgaggag ccagtgggcg atggagttcc attgggagg                              39

<210> SEQ ID NO 42
<211> LENGTH: 51
<212> TYPE: DNA
<213> ORGANISM: Artificial sequence
<220> FEATURE:
<223> OTHER INFORMATION: synthetic DNA

<400> SEQUENCE: 42
aattctaata cgactcacta tagggagaat cttaggtcca ggcagtgccc c                51

<210> SEQ ID NO 43
<211> LENGTH: 51
<212> TYPE: DNA
<213> ORGANISM: Artificial sequence
<220> FEATURE:
<223> OTHER INFORMATION: synthetic DNA

<400> SEQUENCE: 43
aattctaata cgactcacta tagggagacc aatcttaggt ccaggcagtg c                51

<210> SEQ ID NO 44
<211> LENGTH: 51
<212> TYPE: DNA
<213> ORGANISM: Artificial sequence
<220> FEATURE:
<223> OTHER INFORMATION: synthetic DNA

<400> SEQUENCE: 44
aattctaata cgactcacta tagggagaaa ctcagcacca agactaaatt t                51

<210> SEQ ID NO 45
<211> LENGTH: 51
<212> TYPE: DNA
<213> ORGANISM: Artificial sequence
<220> FEATURE:
<223> OTHER INFORMATION: synthetic DNA

<400> SEQUENCE: 45
aattctaata cgactcacta tagggagaca aaactcagca ccaagactaa a                51
```

```
<210> SEQ ID NO 46
<211> LENGTH: 51
<212> TYPE: DNA
<213> ORGANISM: Artificial sequence
<220> FEATURE:
<223> OTHER INFORMATION: synthetic DNA

<400> SEQUENCE: 46
aattctaata cgactcacta gggagact atgaaccagc ctaccttggc g          51

<210> SEQ ID NO 47
<211> LENGTH: 51
<212> TYPE: DNA
<213> ORGANISM: Artificial sequence
<220> FEATURE:
<223> OTHER INFORMATION: synthetic DNA

<400> SEQUENCE: 47
aattctaata cgactcacta gggagata cctatgaacc agcctacctt g          51

<210> SEQ ID NO 48
<211> LENGTH: 51
<212> TYPE: DNA
<213> ORGANISM: Artificial sequence
<220> FEATURE:
<223> OTHER INFORMATION: synthetic DNA

<400> SEQUENCE: 48
aattctaata cgactcacta gggagaac tcaacacaac agagggccgt a          51

<210> SEQ ID NO 49
<211> LENGTH: 51
<212> TYPE: DNA
<213> ORGANISM: Artificial sequence
<220> FEATURE:
<223> OTHER INFORMATION: synthetic DNA

<400> SEQUENCE: 49
aattctaata cgactcacta gggagagg gactcaacac aacagagggc c          51

<210> SEQ ID NO 50
<211> LENGTH: 51
<212> TYPE: DNA
<213> ORGANISM: Artificial sequence
<220> FEATURE:
<223> OTHER INFORMATION: synthetic DNA

<400> SEQUENCE: 50
aattctaata cgactcacta gggagagc agaagacctt ctctctccca g          51

<210> SEQ ID NO 51
<211> LENGTH: 51
<212> TYPE: DNA
<213> ORGANISM: Artificial sequence
<220> FEATURE:
<223> OTHER INFORMATION: synthetic DNA

<400> SEQUENCE: 51
aattctaata cgactcacta gggagagt tgcagaagac cttctctctc c          51

<210> SEQ ID NO 52
<211> LENGTH: 51
<212> TYPE: DNA
<213> ORGANISM: Artificial sequence
<220> FEATURE:
```

-continued

```
<223> OTHER INFORMATION: synthetic DNA

<400> SEQUENCE: 52
aattctaata cgactcacta tagggagatc actctctgtg cactttctga g          51

<210> SEQ ID NO 53
<211> LENGTH: 51
<212> TYPE: DNA
<213> ORGANISM: Artificial sequence
<220> FEATURE:
<223> OTHER INFORMATION: synthetic DNA

<400> SEQUENCE: 53
aattctaata cgactcacta tagggagatc ctcactctct gtgcactttc t          51
```